(12) United States Patent
Knapp

(10) Patent No.: US 10,279,007 B2
(45) Date of Patent: May 7, 2019

(54) TOPICAL TREATMENT METHOD FOR HEALING WOUNDS, DISINFECTING, COVERING AND CONCEALING THE WOUND UNTIL HEALING OCCURS

(75) Inventor: Barry Knapp, Commerce, CA (US)

(73) Assignee: OXYGENETIX INSTITUTE, INC., Reno, NV (US)

( * ) Notice: Subject to any disclaimer, the term of this patent is extended or adjusted under 35 U.S.C. 154(b) by 622 days.

(21) Appl. No.: 12/927,398

(22) Filed: Nov. 15, 2010

(65) Prior Publication Data

US 2012/0164248 A1    Jun. 28, 2012

(51) Int. Cl.
| | |
|---|---|
| *A61Q 1/02* | (2006.01) |
| *A61Q 19/00* | (2006.01) |
| *A61K 36/886* | (2006.01) |
| *A61Q 17/00* | (2006.01) |
| *A61K 8/29* | (2006.01) |
| *A61K 8/891* | (2006.01) |
| *A61K 8/92* | (2006.01) |
| *A61K 8/04* | (2006.01) |
| *A61K 31/047* | (2006.01) |
| *A61K 31/05* | (2006.01) |

(52) U.S. Cl.
CPC ............ *A61K 36/886* (2013.01); *A61K 8/042* (2013.01); *A61K 8/29* (2013.01); *A61K 8/891* (2013.01); *A61K 8/922* (2013.01); *A61K 31/047* (2013.01); *A61K 31/05* (2013.01); *A61Q 1/02* (2013.01); *A61Q 17/00* (2013.01); *A61Q 17/005* (2013.01); *A61Q 19/00* (2013.01); *A61K 2800/31* (2013.01)

(58) Field of Classification Search
CPC .. A61K 2800/31; A61K 31/047; A61K 31/05; A61K 36/886; A61K 8/042; A61K 8/29; A61K 8/891; A61K 8/992; A61Q 17/00; A61Q 17/005; A61Q 19/00; A61Q 1/02
See application file for complete search history.

(56) References Cited

U.S. PATENT DOCUMENTS

| | | | |
|---|---|---|---|
| 4,178,372 A | 12/1979 | Coats | |
| 5,023,090 A | 6/1991 | Levin | |
| 5,776,494 A | 7/1998 | Guskey et al. | |
| 6,060,072 A | 5/2000 | Konik et al. | |
| 6,210,695 B1 | 4/2001 | Beerse et al. | |
| 6,303,105 B1 | 10/2001 | Shah et al. | |
| 6,426,079 B1 * | 7/2002 | Bara | A61K 8/064 424/401 |
| 6,511,672 B2 | 1/2003 | Tan et al. | |
| 6,524,568 B2 | 2/2003 | Worden | |
| 6,555,118 B1 | 4/2003 | Niazi | |
| 6,576,618 B1 | 6/2003 | Herndon et al. | |
| 6,585,969 B1 | 7/2003 | Van Bossuyt | |
| 6,596,703 B1 | 7/2003 | Seed et al. | |
| 6,638,909 B1 | 10/2003 | Grady et al. | |
| 6,689,351 B1 | 2/2004 | Pierce et al. | |
| 6,696,433 B2 | 2/2004 | Ferguson et al. | |
| 6,713,084 B1 | 3/2004 | Kuri-Harcuch et al. | |
| 6,720,180 B2 | 4/2004 | Pilcher | |
| 6,747,062 B2 | 6/2004 | Murrell | |
| 6,767,891 B2 | 7/2004 | Zaveri | |
| 6,787,680 B2 | 9/2004 | McGowan et al. | |
| 6,800,278 B1 | 10/2004 | Perrault et al. | |
| 6,808,707 B2 | 10/2004 | Ensley | |
| 6,828,313 B2 | 12/2004 | Fishbein | |
| 6,838,430 B2 | 1/2005 | Arbeit | |
| 6,861,067 B2 | 3/2005 | McGhee et al. | |
| 6,903,078 B1 | 6/2005 | Williams | |
| 6,906,036 B2 | 6/2005 | Quirk et al. | |
| 6,911,437 B2 | 6/2005 | Edwards et al. | |
| 6,919,320 B1 | 7/2005 | Von Borstel et al. | |
| 7,011,965 B2 | 3/2006 | Kiss | |
| 7,022,675 B2 | 4/2006 | Rodgers | |
| 7,041,312 B2 | 5/2006 | Ehringer | |
| 7,060,795 B2 | 6/2006 | Quirk | |
| 7,071,166 B2 | 7/2006 | Nishida | |
| 7,081,240 B1 | 7/2006 | Akella et al. | |
| 7,083,806 B2 | 8/2006 | Rippon et al. | |
| 7,098,189 B2 | 8/2006 | Malik | |
| 7,101,863 B2 | 9/2006 | Dahricorreia et al. | |
| 7,105,481 B2 | 9/2006 | Uutela et al. | |
| 7,112,342 B2 | 9/2006 | Worden | |
| 7,157,439 B2 | 1/2007 | Boudreau et al. | |
| 7,189,746 B2 | 3/2007 | Weinstein | |

(Continued)

FOREIGN PATENT DOCUMENTS

| | | |
|---|---|---|
| CA | 2325337 A1 * | 5/2001 |
| WO | 99/66526 A1 | 12/1999 |
| WO | WO 01/97610 A1 * | 12/2001 |

OTHER PUBLICATIONS

12927398—Wikipedia: "Benzyl alcohol". Downloaded From WW_25FEB2013.*
C. Viseras; C. Aguzzi; P. Cerezo; A. Lopez-Galindo "Uses of clay minerals in semisolid health care and therapeutic products" Applied Clay Science, 2007 (epub. Oct. 13, 2006), 36, p. 37-50. doi:10.1016/j.clay.2006.07.006.*
Adina Cosmetic Ingredients Ltd. "Gel Base" <URL:www.cosmeticingredients.co.uk/ingredient/gelbase0>, archived online Jul. 28, 2005, 2 pages.*

(Continued)

*Primary Examiner* — Aaron J Kosar
(74) *Attorney, Agent, or Firm* — Holland & Hart

(57) ABSTRACT

A wound healing formulation is disclosed using an oil in water emulsion that uses unpolluted forms of water derived from botanical sources and yeast derived wound healing factors together with natural based disinfectants derived from thymol. As opposed to conventional water supplies, the water derived from botanical sources has factors that contribute to the healing process. The formulation is non-occlusive, allowing the skin to breathe, and contains pigments that conceal the wound.

5 Claims, No Drawings

(56) References Cited

U.S. PATENT DOCUMENTS

| | | |
|---|---|---|
| 7,196,162 B2 | 3/2007 | Quirk et al. |
| 7,198,807 B2 | 4/2007 | Anderson et al. |
| 7,199,159 B2 | 4/2007 | Potier |
| 7,202,226 B2 | 4/2007 | Murray et al. |
| 7,217,417 B2 * | 5/2007 | Knapp .................. A61K 31/01 424/195.16 |
| 7,247,620 B2 | 7/2007 | Morishita et al. |
| 7,255,988 B2 | 8/2007 | Halle et al. |
| 7,282,208 B2 | 10/2007 | Kim |
| 7,410,661 B2 | 8/2008 | Haskell |
| 7,429,252 B2 | 9/2008 | Sarangapani |
| 7,452,864 B2 | 11/2008 | Ståhle-Bäckdahl et al. |
| 7,459,541 B2 | 12/2008 | Hall et al. |
| 7,488,719 B1 | 2/2009 | Decarlo et al. |
| 7,520,866 B2 | 4/2009 | Stenzler et al. |
| 7,524,814 B2 | 4/2009 | Engelmayer et al. |
| 7,572,452 B2 | 8/2009 | Kim |
| 7,588,758 B2 | 9/2009 | O'Connor |
| 7,638,484 B2 | 12/2009 | Braiman-Wiksman et al. |
| 7,709,447 B2 | 5/2010 | Hacket et al. |
| 7,718,176 B2 | 5/2010 | Heavner et al. |
| 7,727,520 B2 | 6/2010 | Ferguson |
| 7,732,574 B2 | 6/2010 | Kelly et al. |
| 7,732,655 B2 | 6/2010 | Cullen et al. |
| 7,736,636 B2 | 6/2010 | Mousa et al. |
| 2002/0025303 A1 * | 2/2002 | Fructus .................. A61K 8/066 424/78.03 |
| 2004/0018161 A1 | 1/2004 | Shah et al. |
| 2004/0101515 A1 * | 5/2004 | Knapp .................. A61K 31/01 424/93.5 |
| 2004/0265344 A1 | 12/2004 | Zolotariov et al. |
| 2008/0253976 A1 * | 10/2008 | Scott .................... A61K 8/0216 424/49 |
| 2009/0143714 A1 * | 6/2009 | Millikin .................. A61K 8/35 604/20 |

OTHER PUBLICATIONS

"ChemicalBook, 4-Isopropyl-3-methylphenol, 2016", http://www.chemicalbook.com/Chemicalproductproperty_EN_CB2491615, pp. 1-2.

U.S. Appl. No. 10/440,990, Final Office Action, dated Apr. 20, 2006, 17 pages.

U.S. Appl. No. 10/440,990, Non-Final Office Action, dated Jul. 28, 2005, 15 pages.

U.S. Appl. No. 14/079,617, Final Office Action, dated Feb. 22, 2016, 12 pages.

U.S. Appl. No. 14/079,617, Non-Final Office Action, dated May 5, 2015, 23 pages.

U.S. Appl. No. 14/079,617, Non-Final Office Action, dated Nov. 29, 2016, 25 pages.

Khanna, et al., "Dermal Wound Healing Properties of Redox-Active Grape Seed Proanthocyanidins", Free Radical Biology and Medicine, vol. 33, Issue 8, Oct. 15, 2002, pp. 1089-1096.

* cited by examiner

TOPICAL TREATMENT METHOD FOR HEALING WOUNDS, DISINFECTING, COVERING AND CONCEALING THE WOUND UNTIL HEALING OCCURS

FIELD OF THE INVENTION

The present invention involves compositions and formulations applied to skin for both cosmetic and healing functions.

DESCRIPTION OF THE RELATED ART

Physicians prescribe wound healing ointments and creams to protect and heal wounds caused by injury or intentionally by surgery. Swelling, bruising, or scars result from the injury or plastic surgery and it may take weeks and months before such effects disappear and there is a need for a cosmetic to conceal such wounds until healing can occur. This concealer also needs to have wound healing factors present. Petrolatum based ointments serve to provide a protective barrier but do not allow the skin to breath. Water and oil emulsion creams contain moisturizers but usually not active ingredients for promoting healing. However, numerous active healing agents are described in the patent art such as nicotinic acid, antibiotics, antioxidants, extracts of various herbs, steroids, genetically engineered polypeptides, nitric oxide, enzymes, matrix metalloproteinase inhibitors, honey and similar substances.

Aloe Barbadensis gel, popularly known as Aloe vera, has a tradition and long use of wound healing, see: "Anti-inflammatory and wound healing activity of a growth substance in Aloe vera," Davis, R H: Donato, J J: Hartman, G M: Haas, R C.: J-Am-Podiatr-Med-Assoc. 1994 February; 84(2): 77-81. Aloe accelerates wound healing when compared with mafenide, see "Beneficial effect of Aloe on wound healing in an excisional wound model." Heggers J P, Kucukcelebi A, Listengarten D, Stabenau J, Ko F, Broemeling L D, Robson M C, Winters W D, J. Altern Complement Med. 1996 Summer; 2(2):271-7. This effect appears to be due to an increased collagen activity, which is enhanced by a lectin, consequently improving the collagen matrix and enhancing the breaking strength of the scar.

As the gel is a watery liquid it can be used in lieu of any commercially derived water for the making of a water in oil emulsion for topical wound use.

Normal process water used for manufacture of cream and lotions is municipal water supply that has been derived from river or lake sources, subject to agricultural runoff that is contaminated by pesticides. The water is filtered and chlorinated to disinfect it and the chlorination of mud related organic components in the water imparts chlorine by products such as chloroform, a carcinogen, to the water. See: "Formation of chloroform by aqueous chlorination of organic compounds", Chaidou, V. I. Georgakilas, C. Stalikas, M. Sarçi and E. S. Lahaniatis, Chemosphere Volume 39, Issue 4, August 1999, Pages 587-594. Chlorination of municipal water is mandated.

Water derived from the Aloe plant is very pure and relatively uncontaminated by comparison. Likewise many water retaining plants can be used as a source of pure water, but Aloe has the most traditional use.

The adaptive skin respiratory factors in cerevisiae lysate can be extracted from the nucleuses of yeast or *Saccharomyces cerevisiae* cells after the yeast has been cultured in nutritional media and then stressed by any stress factor, examples, heat, oxidant or UV radiation. Irradiation and especially elevated temperatures produce stressed proteins in all cells, see (Demple, B. 1998). Signal transduction: a bridge to control, Science 279(5357) 1655). These stresses cause cellular proteins to lose their three-dimensional structure, and the adapting yeast cells produce heat stress proteins that are capable of restoring them to the original configuration. If the protoplasm of the cell is concentrated, a yeast extract may be obtained called Adapted Yeast Extract or AYE. It can be prepared as an alcohol extract of viable *Saccharomyces* lysate. By normalizing the structure of matrix cells, AYE stimulates wound oxygen consumption, epitheliazation, and collagen synthesis. In topical preparations, AYE is characterized and quantified in terms of skin respiratory ability, which is the increased ability to utilize oxygen and produce extracellular matrix. AYE-biofactors extracted from *Saccharomyces cerevisiae* also contain nutrients such as peptides, proteins, amino acids, minerals carbohydrates, nucleic acid and other genetic products. After processing, AYE-biofactors are clear and sediment-free, retaining the active components without the dark color or odor of the starting material see (Fishman, H. M. 2001 "Yeast Has Applications In The Cosmetics Industry", HAPPI, July, 42), see also Lods, L., D. Scholz, C. Dres, C. Johnson & G. Brooks. 2000, "Peroxide-Inducible Protective Factors Produced by *Saccharomyces Cerevisiae*," Cosmet & Toil 115(12) 61-6. See also Fishman, H. M. 2001, "Yeast Has Applications In The Cosmetics Industry", HAPPI, July, 42). Further, when delivered to the lower strata of the skin, AYE biofactors stimulate oxygen consumption by viable cells, causing cellular proliferation and collagen and elastin synthesis.

Furthermore the present invention includes the use of naturally based materials to prevent infection in the wound. One such material is o-cymen-5-ol which is a homologue of thymol, the active constituent of *Thymus vulgaris* or Thyme oil. One provider of this material is Barnett Products Corp. under the name of NET DTB. It kills yeast, mould and bacteria and is a natural replacement for triclosan. It has a minimum growth inhibitory concentration against bacterial species, yeast, and mold of 0.01% which is superior to parabens, salicylic acid, and benzoic acid. The inhibitory values were provided by Barnett Products Corporation, Englewood Cliffs, N.J. 07632. It's safety has been assessed as safe up to 0.5% and typical use is 0.1%.

SUMMARY OF THE INVENTION

The present invention uses a gel based formulation that is non-clogging to the skin using cervitae with a plant based source of water and natural based preservative which simultaneously serves as a disinfectant, includes a vegetable oil, and also contains iron oxides and titanium oxide as wound concealing pigments and it is also well suited for use during the recovery phase following a surgical procedure.

DETAILED DESCRIPTION OF THE PREFERRED EMBODIMENT

The formulation is prepared as follows: Into a suitable container A, add the following: Isododecane (Fanning Corp) 14%, butylenes ethylene/propylene copolymer (Arch Personal Care) 4%, cyclopentasiloxane and PEG/PPG-20 dimethicone (Botanigenics Inc) 5.00%, grape seed oil 1.00%, Dioctyl dodecanedioate (Arch Personal care) 2.00%.

Disperse the following pigments into container A with thorough stirring until all pigments are thoroughly dispersed:

1 Titanium dioxide coated with methicone R434 (Sensient Cosmetic Technologie) 9.35%, yellow iron oxide coated with methicone R0242 (Sensient Cosmetic Technologie) 0.75%, red iron oxide coated with methicone R0241 (Sensient Cosmetic Technologie), 0.28%, black iron oxide coated with methicone R0243 (Sensient Cosmetic Technologie) 0.05%.

The pigments percentages can vary from 0.01 to 3% to match the color of the patients skin.

2 When pigment mixture is homogenous cyclopentasiloxane and disteardimonium hectorite (Elementis Corp) 1.50% and silica (Cabo Sil Corp) can be mixed in until the mixture is homogenous.

In a separate container B combine the following two ingredients with heating at 40 to 50° C. and stir until all solid is dissolved. Butylene Glycol, 2.50% and o-cymen-5-ol (Barnett products NET DTB) 0.10%.

Add this to container A and stir till mixed.

In suitable container C mix the following; Aloe vera gel (Aloecorp 49.5%), Ceravitae (Oxygenetix) 2.80% and salt 1.0%. Ceravitae is a product manufactured by Oxygenetix Institute, Inc. The Aloe percentage may be lessened or increased depending on the percentage of iron oxides in order to make the total percentage 100%. When mixed add slowly to container A and stir with a sweep rotor until a homogenous cream is formed.

Those of ordinary skill in the art will appreciate that the commercially available ingredients listed above are exemplary only, and that the elements in the formulation may be obtained using ingredients other than those listed above. In addition those of ordinary skill in the art will appreciate that the amount of any ingredient or ingredients listed above can be varied depending on the desired thickness, consistency and spread ability of the final product.

This unique combination of ingredients allows the skin to appear undamaged while simultaneously applying healing factors to the damaged skin or wound.

What is claimed is:

1. A wound concealing cosmetic composition comprising a mixture of:
    at least 49.5% Aloe vera gel by weight of the composition;
    wound concealing pigments comprising, by weight of the composition:
        titanium dioxide coated with methicone in an amount of 6.35 to 12.35%;
        yellow iron oxide coated with methicone in an amount of 0 to 3.75%;
        red iron oxide coated with methicone in an amount of 0 to 3.28%; and
        black iron oxide coated with methicone in an amount of 0 to 3.05%;
    water obtained from an Aloe vera plant;
    a disinfectant including a therapeutically effective amount of o-cymen-5-ol;
    butylene glycol;
    isododecane;
    butylene/ethylene/propylene copolymer;
    cyclopentasiloxane;
    PEG/PPG dimethicone;
    grape seed oil;
    dioctyldodecanedioate; and
    salt,
wherein the composition is in a topical dosing form selected from the group consisting of an ointment, a cream, and an emulsion.

2. The wound concealing cosmetic of claim 1, further comprising an amount of disteardimonium hectorite.

3. The wound concealing cosmetic composition of claim 2, comprising said disteardimonium hectorite in an amount of 1.5% by weight of the composition.

4. The wound concealing cosmetic of claim 1, further comprising an amount of silica.

5. The wound concealing cosmetic composition of claim 1, comprising, by weight of the composition:
    0.1% o-cymen-5-ol;
    2.5% butylene glycol;
    14% isododecane;
    4% butylene/ethylene/propylene copolymer;
    5% cyclopentasiloxane and PEG/PPG dimethicone;
    1% grape seed oil;
    2% dioctyldodecanedioate; and
    1% salt.

* * * * *